United States Patent [19]
Pike et al.

[11] Patent Number: 6,143,280
[45] Date of Patent: Nov. 7, 2000

[54] COLOR CONTAINING SILICA RESISTANT TO DYE MIGRATION AND METHOD OF MAKING THE SAME

[75] Inventors: Kathleen S. Pike; John A. Kostinko, both of Bel Air, Md.

[73] Assignee: J. M. Huber Corporation, Edison, N.J.

[21] Appl. No.: 09/314,414

[22] Filed: May 18, 1999

[51] Int. Cl.[7] .............................. A61K 7/16; A61K 47/00; C04B 14/04; C07B 14/04

[52] U.S. Cl. ........................... 424/49; 424/417; 424/724; 514/770; 51/308; 433/435; 433/439; 106/482; 8/523

[58] Field of Search .............................. 424/49–58, 417, 424/724; 514/770; 51/308; 433/435, 439; 106/482

[56] References Cited

U.S. PATENT DOCUMENTS

| | | | |
|---|---|---|---|
| 3,656,981 | 4/1972 | Besohke et al. | 106/288 |
| 3,716,388 | 2/1973 | Lopez et al. | 106/289 |
| 3,728,446 | 4/1973 | Roberts et al. | 424/49 |
| 4,084,983 | 4/1978 | Bernhard | 106/289 |
| 4,167,422 | 9/1979 | Bellanca | 106/289 |
| 4,323,554 | 4/1982 | Bernhard | 106/291 |
| 4,444,746 | 4/1984 | Harvey et al. | 424/49 |
| 4,664,907 | 5/1987 | Muller et al. | 424/52 |
| 4,704,270 | 11/1987 | Muller et al. | 424/49 |
| 4,814,160 | 3/1989 | Carter et al. | 424/7.1 |
| 4,968,351 | 11/1990 | Ahmed et al. | 106/402 |
| 5,074,917 | 12/1991 | Persello et al. | 106/436 |
| 5,127,952 | 7/1992 | Persello et al. | 106/492 |
| 5,318,628 | 6/1994 | Matijevic et al. | 106/499 |
| 5,344,489 | 9/1994 | Matijevic et al. | 106/442 |
| 5,599,525 | 2/1997 | Hsu et al. | 424/49 |
| 5,756,073 | 5/1998 | Miller et al. | 424/49 |
| 5,871,872 | 2/1999 | Matijevic et al. | 430/7 |
| 5,876,701 | 3/1999 | Wong et al. | 424/49 |
| 5,885,343 | 3/1999 | Cernigliaro et al. | 106/482 |

*Primary Examiner*—Shep K. Rose
*Attorney, Agent, or Firm*—Carlos Nieves

[57] ABSTRACT

There is provided a method of adhering dye to a silica. The method comprises providing a silica slurry which includes a plurality of silica particles, depositing alum in the pores of the silica particles, reacting a base with the alum to convert the alum into aluminum hydroxide resulting in treated silica particles. The treated silica particles are then filtered and washed. Thereafter, a dye is mixed with the treated silica particles. The resultant dyed silica product is resistant to dye migration.

17 Claims, 2 Drawing Sheets

COLOR CONTAINING SILICA RESISTANT TO DYE MIGRATION AND METHOD OF MAKING THE SAME

TECHNICAL FIELD

This invention relates to a color containing silica resistant to dye migration and, more particularly, to such a silica for use as a colorant in various formulations particularly dentifrices. The invention also relates to a method of making the color containing silica.

BACKGROUND OF THE INVENTION

Color has long been used to impart a distinctive and aesthetically pleasing appearance to a number of products including toothpastes, coatings, inks and cosmetics. Color is typically provided to such products during the manufacture of the same by admixing in appropriate dyes. Food, Drug and Cosmetic (FD&C) and Drug and Cosmetic (D&C) colors in the United States are water soluble. Accordingly, when such colors are added to products that have a high water content, such as toothpaste formulations, the desired color spreads and uniformly covers the entire product.

Some toothpaste (or other dentifrice) formulations include separate and distinct color components. The colored component can be in the form of speckles that are added to a clear gel or white component to impart a speckled appearance. The colored component could also be in the form of a stripe that is maintained in a discrete layered phase from the white base component. Previous experimentation has shown that the color from water soluble dyes in the colored component of a speckled or striped toothpaste formulation "bleed" into the white or clear gel surrounding component, thereby discoloring the same.

Colorant alternatives to water soluble dyes include pigments. A pigment is generally defined as a finely powdered insoluble material that is dispersed and suspended in the medium to be colored. Pigments are more resistant to color migration when utilized in toothpaste formulations since they consist of water insoluble materials. However, pigments cannot be used in dentifrices in many countries, including the United States, due to safety concerns.

Additional colorant alternatives to the water soluble dyes are "lake pigments." A lake pigment is a term used to define a composition that contains a water-soluble dye and a water-insoluble component to which the dye is chemically bound. The water-insoluble component is typically a metal oxide such as CaO or $Al_2O_3$. A drawback associated with existing lake pigments is that, while more color stable than dyes, unacceptable levels of dye migration are exhibited in many applications. For example, a known technique for providing color in a toothpaste formulation is to introduce a lake pigment into a component of a dentifrice formulation. However, color from the lake pigments typically bleed over time and discolor the white component of the dentifrice. This color migration ruins the aesthetic appeal of the dentifrice.

Another technique for providing a striped toothpaste is to physically separate the different colored toothpaste components in different compartments of a toothpaste tube or dispenser. The different colored components do not contact each other until dispensed from the package. Use of this specialized packaging is expensive.

SUMMARY OF THE INVENTION

The present invention is designed to overcome the deficiencies of the prior art discussed above. It is an object of the invention to provide a color containing silica that is resistant to dye migration.

It is a further object of the invention to provide a method of making such a silica.

In accordance with the illustrative embodiments and demonstrating features of the present invention, there is provided a method of adhering dye to a silica. The method comprises providing a silica slurry which includes a plurality of silica particles, depositing alum in the pores of the silica particles, reacting a base with the alum to convert the alum into aluminum hydroxide. The treated silica particles are then filtered and washed. Thereafter, a dye is mixed with the treated silica particles. It is believed the aluminum hydroxide in the pores of the treated silica particles reacts with the dye resulting in a color containing silica that is resistant to dye migration.

The invention also encompasses a color containing silica produced in accordance with the above-described method.

DETAILED DESCRIPTION OF PREFERRED EMBODIMENTS

In accordance with the preceding summary, the present invention is directed toward a method of incorporating a dye in a silica. More particularly, a method of introducing a lake pigment into the pores of silica particles that significantly reduces dye migration is disclosed. The method comprises providing a slurry which includes a plurality of silica particles. It should be noted that the silica, which is slurried with water, must have a pore structure that is capable of absorbing and retaining alum therein and such silica must be insoluble at a pH of about 3, but otherwise may be of any known type. The pH requirement is necessary since the addition of alum, as described below, drops the pH of the slurry to about 3. Very low structure to very high structure silicas, as described in "Cosmetic Properties and Structure of Fine-Particle Synthetic Silicas", J. Soc. Cosmet, Chem., 29, 497–521, August 1978, the contents of which are incorporated herein by reference, can be used. The preferred silica is an amorphous, precipitated silica having an oil absorption of at least 50 cc/100 g as measured by linseed oil absorption.

A solution of alum $(Al_2(SO_4)_3.14H_2O)$ is then added to the silica slurry and is absorbed (deposited) in the pores of the silica particles. (The quantity of alum utilized determines the color intensity development.) Thereafter, a base, preferably a solution of sodium carbonate, is introduced into the slurry. In the preferred embodiment, the base is added to the slurry containing alum filled silica particles until a pH of about 5 to about 7 is obtained. The base reacts with the alum converting the same to aluminum hydroxide. The reaction between the acidic alum and the basic sodium carbonate can be represented generally by the following equation:

Accordingly, the alum in the pores of the silica particles is converted into aluminum hydroxide after the introduction of the sodium carbonate. The aluminum hydroxide in the pores of the silica is in a gel form. It should be noted that if aluminum hydroxide is introduced into a silica slurry, the aluminum hydroxide would only coat the outside of the silica particles and not enter the particle pores. The present method allows aluminum hydroxide to be directly formed in the pores of the silica particles. As more fully described below, such process results in treated silica particles that are capable of readily reacting with and retaining dyes therein.

The treated silica particles, i.e. aluminum hydroxide filled silica particles, are then filtered and washed. In the preferred embodiment, the treated silica particles are filtered and washed until the filtrate has a conductivity of 500–5000 $\mu$mhos and, more preferably, about 1900 $\mu$mhos. The conductivity is provided by the sodium sulfate ($Na_2SO_4$) by-product. It has been shown that excessively high amounts of sodium sulfate lead to poor color development. Conversely, if too much washing occurs, dyes are not well fixed and the result is an unacceptable amount of bleeding in toothpaste.

Thereafter, a dye, preferably in solution, is mixed with the treated silica particles in an amount of from about 0.5% to about 5% by weight. The aluminum hydroxide filled pores of the treated silica particles react with the dye resulting in a color containing silica that is resistant to dye migration. Any Food, Drug & Cosmetic (FD&C) or Drug and Cosmetic (D&C) dye can be used (all colors and combination of colors). Accordingly, a wide color range and a wide variety of colors (i.e. blue+yellow=green) can be obtained. The dye is added, in solution, to the washed treated silica in order to obtain a silica with a "lake pigment" in the pores. The dye is preferably added in an excessive amount, preferably about 1% by weight, in order to produce desirable color intensity and development.

The treated silica is then either oven or spray dried to a predetermined moisture level ($M_1$). If oven dried, the treated silica is preferably dried to about 3% moisture by weight. If spray dried, the treated silica is preferably dried to about 5 to about 7% moisture by weight. The upper limit on the drying temperature ($T_1$) is related to the temperature in which the dye will char and discolor. After the step of drying, the silica is preferably milled to a particle size of less than 25 microns, preferably between about 5 and 15 $\mu$m.

The treated silica is then filtered and washed to remove excess dye until little color is seen in the filtrate. The treated silica is preferably washed until <0.1 absorption (ABS) in the filtrate is achieved (determined by monitoring the filtrate by UV/Visible spectrometry at the maximum wavelength of the dye solution used). The treated silica is then dried again to a predetermined moisture level ($M_2$) at a predetermined temperature ($T_2$). It should be noted that during this second drying step, the silica should never be dried to a moisture level less than in the first drying step and the second drying temperature should be lower than the first drying temperature, ($T_2 \leq T_1$, $M_2 \geq M_1$). If the silica is going to be used in the color component of a striped toothpaste formulation it should be preferably milled to a powder, i.e. to a median particle size of less than 25 $\mu$m and preferably from about 5 to about 15 $\mu$m (as measured with a Horiba particle size analyzer). If the silica is to be used as colored speckles in a toothpaste formulation, it is compacted into granules. Thereafter, the silica granules are screened to a size of about −30 mesh (600 $\mu$m) to about +80 mesh (180 $\mu$m).

Figure 1:
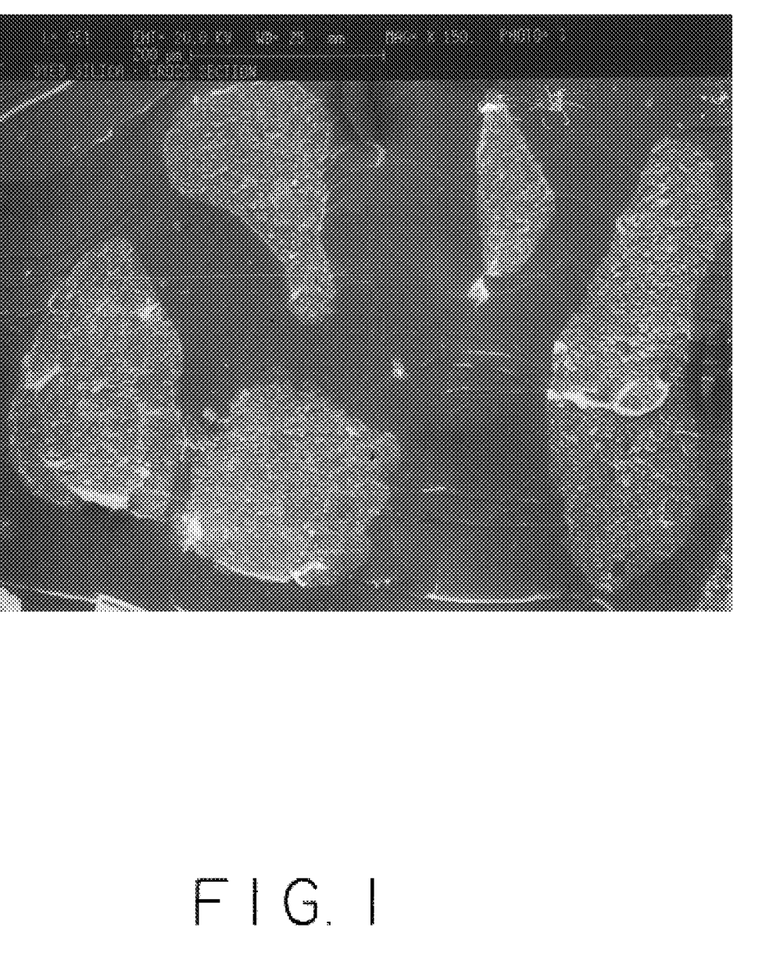
FIG. 1 is a photomicrograph showing several dye containing silica particles in accordance with the present invention.
Figure 2:
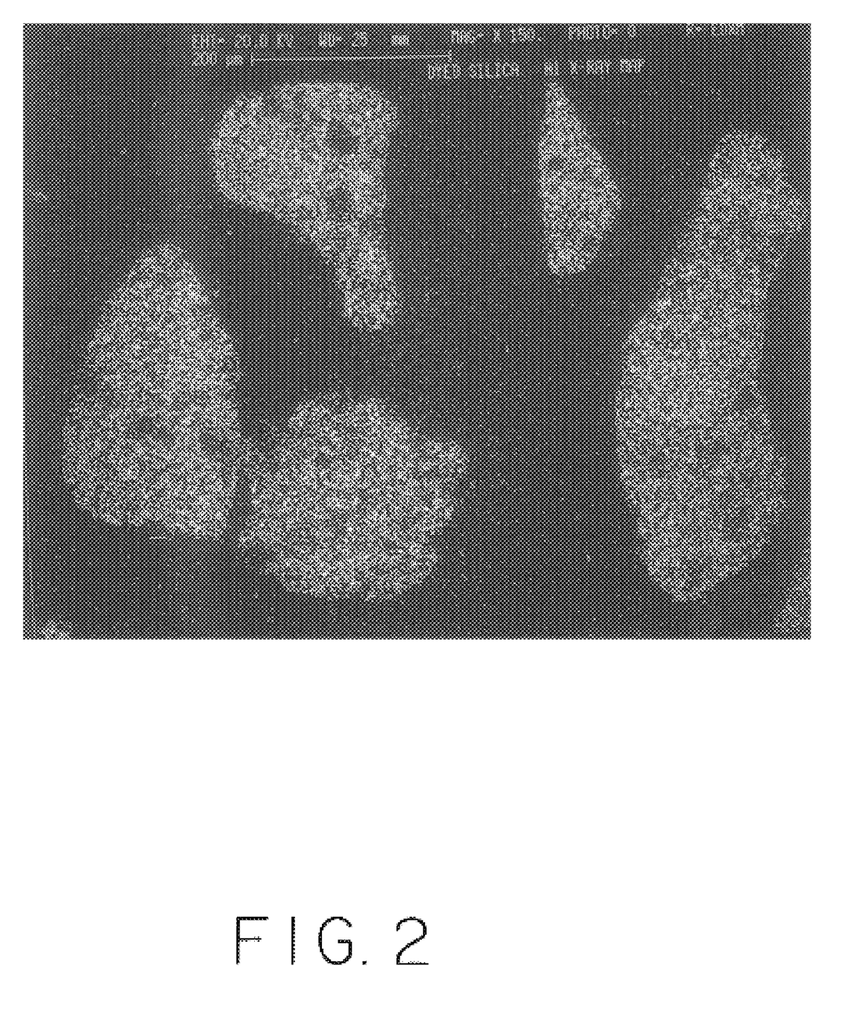
FIG. 2 is an aluminum map of the photomicrograph of FIG. 1 showing aluminum dispersed throughout the silica particles.

As stated above, the resultant color containing silica is resistant to color migration. This can be attributed to the "fixing" of the dye to the aluminum hydroxide gel located in the pores of the individual silica particles. Support for the existence of the aluminum hydroxide gel throughout the silica particles can be found in the two figures. FIG. 1 is a SEM photomicrograph, in cross section, of several dyed silica particles. FIG. 2 is an Al map showing aluminum particles dispersed throughout the silica particles. The aluminum appears as white specs in FIG. 2.

It should be noted that the above process can be practiced on other substrates provided that such substrates include particles with sufficient size and absorption capacity to allow the formation of aluminum hydroxide inside the particles when neutralized by the base and are insoluble at a pH of about 3. Alternate substrates include calcium silicate, sodium aluminosilicate, silica gel and fumed silica. However, precipitated silica is preferred for dentifrice formulations. The color containing product of this invention can additionally be used in other applications where lake pigments are used such as in food, paint, inks, paper, polymers and cosmetics.

Furthermore, instead of alum, any salt that produces a metal hydroxide when neutralized could be utilized such as calcium chloride. Other bases also can be utilized for neutralization such as potassium hydroxide and sodium hydroxide.

While FD&C and D&C dyes are preferred for food and cosmetic applications, it should be noted that any water soluble dye capable of forming a lake pigment could be utilized.

The invention will now be described through illustrative examples. The examples are not intended to limit the scope of the invention defined in the claims appended hereto.

In the following examples, oil absorption, using linseed oil, was determined by the rubout method. This method is based on a principle of mixing oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. Oil absorption is expressed in cc oil per 100 g silica and calculated as follows: Oil absorption=cc oil absorbed/weight of silica, grams×100.

Moisture was determined as percent weight loss after 2 hours in an oven set at 105° C.

Particle size of powders was measured using a Horiba LA-910 particle size analyzer.

EXAMPLE 1

400 grams of a precipitated, amorphous, very high structured silica wetcake (oil absorption of 219) at 13.5% solids available under the trademark Zeodent® 165 from J. M. Huber Corporation of Edison, N.J. (in dried form), was slurried with 150 g of water. 800 g of an 11.85% aqueous solution of alum was added to the slurry at 40 ml/min. Thereafter, an 18% aqueous solution of sodium carbonate was added at 7 ml/min. until the pH of the reaction mixture was 5.9. The reaction mixture was allowed to digest for 45 minutes with agitation and the reaction product was recovered by filtering and washing the same with 1500 ml of warm water. The recovered wetcake was re-slurried with 150 g of water and 200 g of a 1% ED&C Blue No. 1 aqueous solution and the slurry was then mixed for approximately 1.5 hours.

The slurry was then filtered and oven dried at 105° C. overnight. The dried cake of dyed silica was milled, and re-slurried in 3000 ml of water and then filtered and washed to remove excess dye. The dyed silica was again re-slurried in 3000 ml of water and was mixed overnight. Thereafter, the dyed silica was filtered and washed with water until a colorless filtrate (Absorbance less than 0.100) was obtained. The recovered silica product was then oven dried overnight and milled.

A color intensity test was performed on the recovered silica product to determine its color intensity. Specifically, a test utilizing a Gardner XL 835 calorimeter was conducted which comprises measuring the Hunter Scale L, $a_L$, $b_L$ values of a smooth pressed disc of dyed silica. Specifically, 4 gram of dyed silica is pressed at 7000 psi (pressure released soon after 7000 psi is reached) in a 1 inch die in a hydraulic press (Angstrom, Inc., Chicago, Ill., Angstrom model 4451-A.) The pressed disc surface must be smooth. The smooth disc surface is placed over the back port of the previously calibrated (manufacturers directions) calorimeter. L, aL, bL values are recorded.

The color intensity test result for Example 1 color containing silica is provided in Table 1 below.

A screening test is conducted to determine bleeding of colored silica in water. The screening test comprises measuring the visible absorbance of an aqueous filtrate from slurried dyed silica. Specifically, 1.0 gram dyed silica is placed in a 50 ml beaker containing a magnetic stir bar, along with 29 g deionized water. The beaker is placed on a magnetic stir plate and stirred for 10 min. The slurry is then filtered with vacuum on #42 Whatman filter paper (Whatman International Ltd., England). A UV/Visible spectrometer, (Perkin Elmer model Lambda 2) is zeroed with deionized water in both cells. One cuvette is filled with the filtrate obtained above and the reference cuvette is filled with deionized water. Absorbance of the filtrate is measured at the maximum visible wavelength of an aqueous solution of the dye used, i.e. FD&C Blue No. 1 at 628 nm, FD&C red No. 33 at 520 nm. An absorbance reading of 0.100 or less indicates the colored silica product is acceptable and will not bleed when incorporated into a dental formulation. Should the absorbance be greater than 0.100, the colored silica must be rewashed.

Screening test absorbance results for the color containing silica of Example 1 are given in Table 1 below.

EXAMPLE 2

In this example, dried and milled Zeodent® 165 silica was used instead of the Zeodent® wetcake of Example 1. 54 g of Zeodent® 165 silica was slurried with 496 g water. 800 g of an 11.85% aqueous solution of alum was added to the slurry at 30 ml/min. The remainder of the processing steps of Example 1 were followed.

The color intensity and screening test absorbance results for the color containing silica of Example 2 are given in Table 1 below.

EXAMPLE 3

In this example, dried and milled medium structure Zeofree® 153 silica (oil absorption of 178) was used instead of the Zeodent® 165 product of Example 2. The remainder of the processing steps of Example 2 were followed.

The color intensity and screening test absorbance results for the color containing silica of Example 3 are given in Table 1 below.

TABLE 1

|  | Example 1 | Example 2 | Example 3 |
|---|---|---|---|
| Color intensity, | | | |
| L | 70.4 | 73.3 | 76.2 |
| $a_L$ | −14.3 | −13.8 | −13.2 |
| $b_L$ | −26.8 | −24.0 | −24.1 |
| Screening test, Abs. @ 628 nm | 0.068 | 0.066 | 0.097 |

As can be seen in Table 1, Example 1–3 products have strong color intensity as indicated by the $b_L$ values and their screening test values indicate that the products will have an extremely low level of bleeding when incorporated into a dentifrice formulation.

EXAMPLE 4

15 liters of a precipitated, amorphous, low structured silica (oil absorption of 86) wetcake (25.8% solids) available under the trademark Zeodent® 113 from J. M. Huber Corporation of Edison, N.J. (in dried form), was slurried with 31 liters of water with agitation provided by a Cowles mixer. 89 liters of an 12.27% aqueous solution of alum was added to the slurry at 2.5 L/min and the mixture was digested for 20 min with agitation. Thereafter, an 18% aqueous solution of sodium carbonate was added at 0.5 L/min. until the pH of the reaction mixture was 5.9. The reaction mixture was allowed to digest for 30 minutes with agitation. The reaction product (substrate) was recovered by filtering on a plate and frame filter and washing the same with warm water until the conductivity of the filtrate was 1900 μmhos.

Several batches of the above substrate were combined to provide enough substrate to be dyed blue, red and green.
Blue Colored Substrate (Example 4a):

24 kg of substrate was placed in a small drum with 10.285 liters of water. The slurry was mixed (Cowles) until smooth. With the Cowles mixer set on its lowest speed, previously prepared 1% FD&C Blue No. 1 dye solution (13.58 Kg water and 137 g dye powder) was added slowly. The slurry was agitated for 60 minutes then filtered. 1400 g of the recovered product was reslurried with 1800 g water and spray dried. 240 g of the dried product was milled to an average particle size of 17 μm. 214 g of the milled product was washed with warm water until the absorbance (Abs) at 628 nm was below 0.100. The washed blue product was spray dried once again, milled and retained for incorporation as a powder into a striped toothpaste formulation as Example 4a silica. Also, 2.5–3.0 g of the dried milled blue product was pressed at 15,000 psi on an Angstrom hydraulic press fitted with a 1 inch die. The pressed particles were screened on sieves with granules between 250 and 425 μm being retained for incorporation into a speckled toothpaste formulation as Example 4a silica.
Red Colored Substrate (Example 4b)

350 g of the above undyed substrate was reslurried with 150 g of water with agitation. 200 g of 1% FD&C Red No. 33 was added and the slurry was mixed for 1 hour. The slurry was filtered on a 15 cm Buchner filter flask with No. 4 Whatman filter paper and the recovered wetcake was dried in an oven at 105° C. overnight. The dried cake was milled and then washed with water until the filtrate absorbance at 520 nm was less than 0.100. The recovered washed wetcake was dried at 105° C. overnight and milled. Pressed particles were screened on sieves with granules between 250 and 425 μm being retained for incorporation into a speckled toothpaste formulation as Example 4b silica.

Green Colored Substrate (Example 4c)

The same coloring process as used to dye the substrate red in Example 4b above was followed except green dye was substituted for the red dye. The green dye was made by mixing 50 g of a 1% solution of D&C Yellow No. 10 and 150 g of a 1% solution of FD&C Blue No. 1. The dried cake was milled then washed with water until the Absorbance at 410 nm of the filtrate was less than 0.100. Pressed particles were screened on sieves with granules between 250 and 425 μm being retained for incorporation into a speckled toothpaste formulation as Example 4c silica.

Results of the color intensity and screening tests are given in Table 2 below.

TABLE 2

|  | Example 4a | Example 4b | Example 4c |
| --- | --- | --- | --- |
| Color intensity, | | | |
| L | 72.6 | 71.8 | 74.0 |
| $a_L$ | −15.6 | +28.6 | −21.9 |
| $b_L$ | −26.0 | −8.6 | −6.2 |
| Screening test, Abs. @ 628 nm | 0.085 | | |
| Screening test, Abs. @ 520 nm | | 0.090 | |
| Screening test, Abs. @ 410 nm | | | 0.080 |

As can be seen in Table 2 above, Example 4a product has a strong blue intensity ($b_L$=−26.0), Example 4b product a strong red intensity ($a_L$=+28.6) and Example 4c a strong green intensity ($a_L$=−21.9).

EXAMPLE 5

1000 grams of a precipitated, amorphous, very high structured calcium silicate (oil absorption of 475) wetcake at about 20% solids available under the trademark Hubersorb® 600 from J. M. Huber Corporation of Edison, N.J. (in dried form), was slurried with 250 g of water. 250 g of the slurry was weighed into a stainless steel beaker and mixed with 50 ml additional water. The pH of this slurry was 9.75. 50 g of a 47.4% aqueous solution of alum was diluted with 150 ml water and added to the slurry all at once. The slurry was mixed for 1 hour. Thereafter, a saturated aqueous solution of sodium carbonate was added dropwise until the pH of the reaction mixture was 6.0. The reaction mixture was allowed to digest for 2 hours with agitation and the reaction product was recovered by filtering and washing the same with 800 ml of warm water. The recovered wetcake was re-slurried with 50 ml of water and 100 ml of a 1% aqueous solution of FD&C Blue No. 1 and thereafter mixed for approximately 1 hour.

The slurry was then filtered and oven dried at 105° C. overnight. The dried cake of dyed silicate was milled, and re-slurried, filtered and washed until the filtrate was light blue. The dyed silica was again re-slurried, filtered and washed with water until a colorless filtrate was obtained. The recovered silica product was then oven dried overnight and milled.

The color intensity and screening test absorbance results for the color containing calcium silicate of Example 5 are given in Table 3.

TABLE 3

|  | Example 5 |
| --- | --- |
| Color intensity, | |
| L | 72.2 |
| $a_L$ | −14.8 |
| $b_L$ | −23.2 |
| Screening test, Abs. @ 628 nm | 0.064 |

EXAMPLE 6

Colored silicas and silicates of the examples 2, 4 and 5 were incorporated as powders into a striped toothpaste formulation containing one white component and one colored component or as colored granules in a clear gel toothpaste in order to impart a "speckled" appearance. The two toothpaste making procedures are described below. Prepared toothpaste is sealed into plastic toothpaste tubes for storage and held at constant selected temperatures for testing.

Speckled Toothpaste Procedure:

Combine in the order given glycerin, Carbowax, CMC-7MFX and sorbitol and stir until dissolved (A). Separately combine in the order given water, saccharin, sodium MFP, and TSPP and stir until dissolved (B). Combine A and B with stirring to form a "premix". Place the premix into a Ross mixer (model 130LDM, Charles Ross & Co., Haupeauge, N.Y.), add silica thickener and silica abrasive and mix on high speed (63 Hz) without vacuum. Draw 30 inches of vacuum and mix for 15 minutes. Add colored speckles, sodium lauryl sulfate and flavor. Stir for 5 minutes at reduced mixing speed (about 30 Hz).

TABLE 4

Speckled Dentifrice Formulations

|  | Control | Ex. 4a silica | Ex. 4b silica | Ex. 4c silica |
| --- | --- | --- | --- | --- |
| Glycerin, (99.5%), g | 25.00 | 25.00 | 25.00 | 25.00 |
| Sorbitol, (70.0%), g | 38.59 | 38.59 | 38.59 | 38.79 |
| Deionized water, g | 6.00 | 6.00 | 6.00 | 6.00 |
| Carbowax 600, g | 3.000 | 3.000 | 3.000 | 3.000 |
| CMC-7MXF, g | 0.400 | 0.400 | 0.400 | 0.400 |
| Sodium saccharin, g | 0.200 | 0.200 | 0.200 | 0.200 |
| Sodium monofluorophosphate, g | 0.760 | 0.760 | 0.760 | 0.760 |
| Tetrasodium pyrophosphate, g | 0.500 | 0.500 | 0.500 | 0.500 |
| Zeodent ® 165 silica thickener, g | 4.20 | 4.20 | 4.20 | 5.00 |
| Zeodent ® 115 silica abrasive, g | 19.00 | 19.00 | 19.00 | 18.00 |
| Colored speckles, g | 0.50 | 0.50 | 0.50 | 0.50 |
| Sodium laurel sulfate, g | 1.20 | 1.20 | 1.20 | 1.20 |
| Flavor, g | 0.65 | 0.65 | 0.65 | 0.65 |

Carbowax 600 is available from Union Carbide Corporation, Danbury, CT.
CMC-7MXF is carboxymethylcellulose available from Aqualon, division of Hercules Corporation, Wilmington, De.
Zeodent ® 165 and Zeodent ® 115 silicas are available from J. M. Huber Corporation.

Determination of Bleeding of Colored Granules (Speckles) In Clear Get Toothpaste A 10 cc syringe, of which the tip has been cut off so that the end opening is about ¼ inch in diameter, is filled about half full with gel toothpaste containing speckles. The gel toothpaste is pushed by depressing the syringe plunger through a 100 mesh (150 μm) screen onto a sheet of weighing paper. This removes all the colored speckles from the toothpaste. Center a plexiglass microscope slide spacer (38×75 mm, 3 mm thick with a 24×47 mm open space) onto a microscope slide, which is set on a clear flat surface. Fill the spacer with screened gel toothpaste and place another microscope slide on top of the spacer. Slowly apply pressure, by hand, to remove excess air and toothpaste. Hold the slide with the long side horizontally and against the back port of a Gardner XL-835 calorimeter (previously calibrated) allowing light to pass through a part of the slide containing no air bubbles. While maintaining the slide position, cover the slide with the instrument's white calibration tile plate. Record the L, $a_L$ and $b_L$ values.

A zero reading for $a_L$ and $b_L$ lies on the black-white axis, indicates a shade of gray. A plus value of $a_L$ indicates redness and a minus value of $a_L$ indicates greenness. A plus value of $b_L$ indicates yellowness and a minus value of $b_L$ indicates blueness. Bleeding is the migration of color from the colored granules into the clear gel toothpaste. The degree of bleeding is measured by decrease in $b_L$ values for blue colored substrates, by a decrease in $a_L$ values for green dyed substrates and an increase in $a_L$ values for red dyed substrates. The greater the difference in $a_L$ or $b_L$ values from the initial sample measurement to an aged sample measurement, the more bleeding has occurred.

For comparison, a control sample is prepared as follows: 15 g of Zeodent® 113 silica and 0.2 g of purchased FD&C Blue No. 1 aluminum lake (available from Warner Jenkinson Inc., St. Louis, Mo.) were physically dry mixed together. The mixture, which had a $b_L$ value of −27.2, was pressed at 7000 psi. The pressed pellet was screened, and particles between 250 and 425 μm were incorporated into a toothpaste formulation of the type described in Table 4 above.

The toothpaste is tested when initially made and after 1 and 3 weeks storage at room temperature (68° F. or 20° C.) and after 1 and 3 weeks storage at 120° F. (49° C.). Maximum bleed is seen in most speckle toothpaste after it has been stored for 2 weeks at 120° F.

TABLE 5

Speckled Toothpaste Bleeding Results ($a_L$ and $b_L$ values)

|  | Control ($b_L$) | Ex. 4a ($b_L$) | Ex. 4b ($a_L$) | Ex. 4c ($a_L$) |
|---|---|---|---|---|
| 24 hr., 68° F. | −11.4 | 0.5 | +2.5 | −4.7 |
| 1 week, 68° F. | −15.5 | −0.9 | +3.9 | −5.8 |
| 3 weeks, 68° F. | −16.3 | −1.4 | +3.6 | −6.2 |

TABLE 5-continued

Speckled Toothpaste Bleeding Results ($a_L$ and $b_L$ values)

|  | Control ($b_L$) | Ex. 4a ($b_L$) | Ex. 4b ($a_L$) | Ex. 4c ($a_L$) |
|---|---|---|---|---|
| 1 week, 120° F. | −17.3 | −2.2 | +3.6 | −6.5 |
| 3 weeks, 120° F. | −15.3 | −3.9 | +5.3 | −6.5 |

As can be seen in Table 5 above, colored products of the invention bleed much less than the control. In fact, the inventive speckles visually retain their distinctive colored granule shape in toothpaste. By comparison, the colored speckles of the control sample are not visually perceptible because of the discoloration of the toothpaste, due to excessive bleeding.

Striped Toothpaste Procedure

Combine in the order give glycerin, Carbowax, CMC-7MFX and sorbitol and stir until dissolved (A). Thereafter, separately combine water, saccharin, sodium MFP or sodium fluoride, and TSPP in the order given and stir until dissolved (B). Combine A and B with stirring to form a "premix". Place the premix into a Ross mixer and add silica thickener and silica abrasive and mix without vacuum at about 63 Hz. Add colored powder or dye with stirring. Draw 30 inches of vacuum and mix for 15 minutes. Add sodium lauryl sulfate and flavor. Stir for 5 minutes at a reduced mixing speed (about 30 Hz).

Table 6 Striped Dentifrice Formulations

|  | Control for Ex.2 | Ex.2 | Control for Ex.4a | Ex.4a | Control for Ex.5 | Ex.5 |
|---|---|---|---|---|---|---|
| Glycerin, (99.5%), g | 25.00 | 25.00 | 25.00 | 25.00 | 25.00 | 25.00 |
| Sorbitol, (70.0%), g | 39.307 | 39.307 | 38.59 | 38.59 | 39.307 | 39.307 |
| Deionized water, g | 6.00 | 6.00 | 6.00 | 6.00 | 6.00 | 6.00 |
| Carbowax 600, g | 3.000 | 3.000 | 3.000 | 3.000 | 3.000 | 3.000 |
| CMC-7MXF, g | 0.400 | 0.400 | 0.400 | 0.400 | 0.400 | 0.400 |
| Sodium saccharin, g | 0.200 | 0.200 | 0.200 | 0.200 | 0.200 | 0.200 |
| Sodium monofluorophosphate, g | 0 | 0 | 0.760 | 0.760 | 0 | 0 |
| Sodium fluoride | 0.243 | 0.243 | 0 | 0 | 0.243 | 0.243 |
| Tetrasodium pyrophosphate, g | 0.500 | 0.500 | 0.500 | 0.500 | 0.500 | 0.500 |
| Zeodent ® 165 silica thickener, g | 5.50 | 5.50 | 4.50 | 3.70 | 5.50 | 5.50 |
| Zeodent ® 115 silica abrasive, g | 17.50 | 14.00 | 19.00 | 19.00 | 18.00 | 16.00 |
| Inventive Colored powder, g | 0 | 4.00 | 0 | 1.00 | 0 | 2.000 |
| 1% FD&C Blue No. 1, g | 0.500 | 0 | 0.200 | 0 | 0.200 | 0 |
| Sodium laurel sulfate, g | 1.20 | 1.20 | 1.20 | 1.20 | 1.20 | 1.20 |
| Flavor, g | 0.65 | 0.65 | 0.65 | 0.65 | 0.65 | 0.65 |

Carbowax 600 is available from Union Carbide Corporation, Danbury, CT.
CMC-7MXF is carboxymethylcellulose available from Aqualon, division of Hercules Corporation, Wilmington, DE.
Zeodent ® 165 and Zeodent ® 115 silicas are available from J. M. Huber Corporation.

Determination of Bleeding of Colored Gel Toothpaste into White Opaque Toothpaste A 10 cc syringe, of which the tip has been cut off so that the end opening is about ¼ inch in diameter, is filled about half full with colored gel toothpaste. Center a plexiglass microscope slide spacer (38×75 mm, 3 mm thick with a 24×47 mm open space) onto a microscope slide, which is setting on a clear flat surface. Squeeze a ribbon of colored gel toothpaste along one 24 mm side of the spacer opening and then squeeze a ribbon of opaque toothpaste along the other 24 mm side of the spacer Place another microscope slide on top of the spacer. Slowly and evenly apply pressure, by hand, to force the two ribbons to meet in the center of the spacer and to remove excess air and toothpaste. Repeat this procedure to produce two pressed slides for each sample. Hold the slide with the long side vertical and the opaque portion toward the top and against the back port of a Gardner XL-835 colorimeter (previously calibrated) allowing light to pass through the gel portion of the slide. Move the slide down until the opaque portion is just covered by the inner circle of light. Record the L, $a_L$ and $b_L$ values of each slide 2–3 times and average the readings. After these initial readings are taken, place both slides in separate self-sealing plastic bags, seal, and store one at room temperature (68° F.) and the other at in an oven set at elevated temperature (120° F.) for aged bleeding tests at 1 and 3 week intervals.

A zero reading for $a_L$ and $b_L$ lies on the black-white axis, indicating a shade of gray. A plus value of $a_L$ indicates redness and a minus value of $a_L$ indicates greenness. A plus value of $b_L$ indicates yellowness and a minus value of $b_L$ indicates blueness. Bleeding is the migration of color from the colored gel into the white opaque toothpaste. The degree of bleeding is measured as the difference in $a_L$ or $b_L$ values, depending on the color used, from the initial reading to the aged samples.

TABLE 7

Striped Toothpaste Bleeding Results ($b_L$ values) using FD & C Blue No. 1 Dye

|  | Control for Ex.2 | Ex.2 | Control for Ex.4a | Ex.4a | Control for Ex.5 | Ex.5 |
| --- | --- | --- | --- | --- | --- | --- |
| Initial, 68° F. | −0.20 | +0.20 | −0.30 | −0.20 | +0.60 | +0.50 |
| 1 week, 68° F. | −2.80 | −0.50 | −0.30 | +0.20 | +0.20 | +0.30 |
| 3 weeks, 68° F. | −2.50 | −0.40 | −0.90 | −0.10 | −1.30 | −0.9 |
| Difference | 2.30 | 0.20 | 0.60 | 0.10 | 1.90 | 1.40 |
| Initial, 120° F. | 0.00 | 0.00 | −0.10 | −0.30 | +0.30 | +0.40 |
| 1 week, 120° F. | 4.90 | −0.90 | −1.40 | −0.30 | −0.90 | −0.50 |
| 3 weeks, 120° F. | −6.20 | −1.40 | −2.80 | −0.50 | −2.60 | −1.70 |
| Difference | 6.20 | 1.40 | 2.70 | 0.20 | 2.90 | 2.10 |

As can be seen from the data above, each of the inventive colored materials bleed much less (as indicated by the smaller difference in $b_L$ values within each temperature aging set) than the controls. Visually, the opaque ribbon discoloration is barely perceptible.

EXAMPLE 7

To show the effect of washing the colored wetcake before drying and the effect of the second drying step temperature on the final product color and stability, a colored low structure silica was prepared utilizing different washing and drying processing steps.

54 grams of a precipitated, amorphous, low structured silica sold under the trademark Zeodent® 113 and manufactured by J. M. Huber Corporation of Edison, N.J., was slurried with 496 g of water. 800 g of an 11.85% aqueous solution of alum was added to the slurry at 60 ml/min. Thereafter, an 18% aqueous solution of sodium carbonate was added at 14 ml/min. until the pH of the reaction mixture was 5.9–6.0. The reaction mixture was allowed to digest for 30 minutes with agitation and the reaction product was recovered by filtering on a Buchner funnel with vacuum and washing the same with 500 ml of warm water. The wetcake was reslurried in 500 ml warm water and mother liquor was added until the conductivity was about 1500 μsiemens. The slurry was mixed for 20 minutes and then filtered. Filtrate conductivity was 1517 μS.

The wetcake collected above was slurried with 200 ml of 1% FD&C Blue No. 1 dye and 150 g water, mixed for 1 hour, and filtered with no washing. 83 g of this wetcake was washed, without prior drying, until the filtrate had an absorbance of less than 0.100. The washed wetcake was dried overnight at 105° C. in an oven and milled to less than 25 μm (Example 8a). Color intensity was measured on Example 8a product. Thereafter the milled material was reslurried in 1 L of water, filtered and washed until the filtrate had an absorbance of less than 0.100. The resultant wetcake was split in half, with one half being dried at 90° C. and the other at 130° C., thereafter both products were milled. The product dried at 90° C. is Example 8b and the product dried at 130° C. is Example 8c. Both products were screened for bleeding and color intensity. Example 8c failed the screening test and therefore was reslurried and washed until the filtrate had an Absorbance of less than 0.100, thereafter dried at 105° C. and milled (Example 8d).

TABLE 8

|  | Process Variables | Filtrate Abs. @ 628 nm | Intensity $b_L$ |
| --- | --- | --- | --- |
| Example 8a | Not dried before washing | 0.024 | −13.7 |
| Example 8b | Dried, washed ($T_2$ = 90° C.) | 0.076 | −28.8 |
| Example 8c | Dried, washed ($T_2$ = 130° C.) | 0.120 | — |
| Example 8d | 8c rewashed ($T_2$ = 105° C.) | 0.030 | −27.4 |

Washing the wetcake before drying it, produces a very light product as indicated by Example 8a with a $b_L$ value of only −13.7. This is compared to a $b_L$ value of −28.8 for the same wetcake which was dried before washing (Example 8b). It is seen from Example 8c that if $T_2$ is greater than $T_1$ (105° C.), the screening test absorbance is greater than 0.100 and the product must be rewashed. It is believed that the aluminum hydroxide gel structure collapses at this higher temperature, forcing more dye out of the substrate pores.

COMPARATIVE EXAMPLE 1

To show that a dry physical blend of a lake pigment and a silica or silicate substrate does not give the same results as the inventive process, an aluminum lake was prepared and blended with a precipitated amorphous silica.

An 18% aqueous solution of sodium carbonate was added at 14 ml/min. to 1600 g of an 11.85% aqueous solution of alum until a pH of 5.9 was reached. The reaction mixture was allowed to digest for 20 minutes with agitation and the reaction product was recovered by filtering on a Buchner funnel with vacuum and washing the same with 500 ml of warm water. The wetcake was reslurried in 500 ml warm water and washed until the conductivity of the filtrate was 400 μmhos. The wetcake collected above was reslurried with 400 g of water and 0.81 g sodium sulfate was added to simulate the amount of sodium sulfate contributed by silica. To this slurry was added 400 g of 1% FD&C Blue No. 1 dye. The slurry was mixed for 1 hour, filtered with no washing, and dried overnight in an oven set at 105° C.

10 g of the blue aluminum lake produced above was dry blended with 40 g of Zeodent® 113 silica for 30 minutes in a pebble mill containing about 15 pebbles. Thereafter, the blended material was reslurried in 1 L warm water, filtered and washed with 500 ml aliquots of water until the absorbance at 628 nm of the filtrate was less than 0.100. Results are given in Table 9 below.

COMPARATIVE EXAMPLE 2

To show that a wet blend of a lake pigment and a silica or silicate substrate does not give the same results as the inventive process, an aluminum lake was prepared and wet blended with a precipitated amorphous silica.

Specifically, to 800 g of a 11.85% aqueous alum solution was added 18% sodium carbonate solution at a rate of 7 ml/min until the pH of the reaction mixture is 5.9. The reaction mixture was allowed to digest with agitation for 20 minutes. The resulting aluminum gel was recovered by filtration on a Buchner funnel and the wetcake washing with water until the conductivity of the filtrate 1500 μmhos. The washing aluminum gel wetcake was reslurried in 100 ml water.

54 g of Zeodent® 113 silica was slurried in 100 ml water. The reslurried aluminum gel prepared above was pumped into the silica slurry at a rate of 15 ml/min, utilizing a peristaltic pump. The resulting slurry was digested for 20 minutes with agitation. The resulting slurry was filtered, reslurried in 150 ml water and 200 ml of a 1% FD&C Blue No. 1 aqueous solution and mixed for 1 hour. The slurry was then filtered and oven dried (105° C.) overnight and milled. The milled product was reslurried in water and then filtered and washed to remove excess dye, and dried overnight at 95° C. Results are given in Table 9 below.

COMPARATIVE EXAMPLE 3

A non-porous silica (finely ground quartz sand, also known as silica flour) was coated with the aluminum gel prepared as in Comparative Example 2. Specifically, 54 g of silica flour was slurried in 400 g water. 200 g aluminum gel was reslurried in 100 ml water and pumped into the silica flour slurry at 15 ml/min. utilizing a peristaltic pump. The resultant mixture was mixed for 15 minutes and filtered. The resultant wetcake was reslurried with 150 ml water and 200 ml of 1% FD&C blue No. 1 dye was added. The slurry was mixed for 1 hour, filtered without washing and dried at 105° C. overnight. The dried colored cake was milled and reslurried in 1000 ml water then filtered and washed until the filtrate absorbance was less than 0.1. The washed wetcake was reslurried, washed, dried overnight at 95° C. and milled. Since the Screening Absorbance test showed an absorbance of 0.247, the product was reslurried, washed and dried again at 95° C. The color intensity and screening test absorbance results for the product of Comparative Example 3 are given in Table 9 below.

The colored silica flour prepared above was pressed at 9000 psi and the pellet obtained was screened to collect particles between 250 and 425 μm. These particles were incorporated into the speckle toothpaste formulation described in Table 4 and evaluated for bleeding. Bleeding results are given in Table 10 below.

TABLE 9

|  | Comp. Ex 1 | Comp. Ex. 2 | Comp. Ex. 3 | Example 4a |
| --- | --- | --- | --- | --- |
| Color intensity, |  |  |  |  |
| L | +82.5 | 66.6 | +51.9 | 72.6 |
| $a_L$ | −7.20 | −14.4 | −11.4 | −15.6 |
| $b_L$ | −12.70 | −30.2 | −35.9 | −26.0 |
| Screening test, Abs. @ 628 nm | 0.060 | 0.086 | 0.082 | 0.085 |

The blue intensity, as indicated by the $b_L$ values, of the dry physical blend of the blue aluminum lake and Zeodent 113 silica product of Comparative Example 1 is less than half that of the Zeodent 113® silica colored by the inventive process (Example 4a). Comparative Example 1 product's color intensity ($b_L$ of −12.70) was not strong enough to be visually apparent in toothpaste. The wet blend of blue aluminum lake and Zeodent 113® silica of Comparative Example 2 had strong blue intensity ($b_L$ of −30.2), but bled excessively when put into toothpaste. In fact, the speckles visually disappeared in 3 weeks. The colored silica flour of Comparative Example 3 had a strong intensity ($b_L$ of −35.9), but likewise bled excessively when put into toothpaste.

TABLE 10

Speckled Toothpaste Bleeding Results ($b_L$ values)

|  | Comp. Ex. 2 ($b_L$) | Comp. Ex. 3 ($b_L$) | Example 4a |
| --- | --- | --- | --- |
| 24 hr., 68° F. | −1.6 | −3.4 | 0.5 |
| 1 week, 68° F. | −3.1 | −4.3 | −0.9 |
| 3 weeks, 68° F. | −4.8 | −8.1 | −1.4 |
| 1 week, 120° F. | −7.5 | −11.1 | −2.2 |
| 3 weeks, 120° F. | −7.8 | −11.1 | −3.9 |

The present invention may be embodied in other specific forms without departing from the spirit or essential attributes thereof and accordingly reference should be made to the appended claims rather than the foregoing specification as indicating the scope of the invention.

What is claimed is:

1. A color containing silica resistant to dye migration comprising:

a plurality of silica particles, each of said silica particles including a plurality of pores, and said plurality of pores being filled with a dye fixed aluminum hydroxide.

2. The color containing silica of claim 1 wherein the silica has a moisture level of less than about 10% by weight.

3. The color containing silica of claim 1 wherein the silica is a precipitated, amorphous silica having an oil absorption of at least about 50 cc/100 g.

4. The color containing silica of claim 1 wherein said dye fixed aluminum hydroxide includes a dye selected from the group consisting of a FD&C dye and a D&C dye.

5. The color containing silica of claim 1 wherein the silica is in powder form with a median particle size of less than about 25 microns.

6. The color containing silica of claim 1 wherein the silica is in granule form with a particle size of from about 180 to about 600 microns.

7. A color containing silicate resistant to dye migration comprising:

a plurality of silicate particles, each of said silicate particles including a plurality of pores, and said plurality of pores being filled with a dye fixed aluminum hydroxide.

8. The color containing silicate of claim 7 wherein said silicate is calcium silicate.

9. The color containing silica of claim 1 wherein said plurality of silica particles comprise amorphous, precipitated silica.

10. The color containing silica of claim 1 wherein said plurality of silica particles comprises silica gel.

11. The color containing silica of claim 1 wherein said plurality of silica particles comprises fumed silica.

12. The color containing silica of claim 1 wherein said dyed fixed aluminum hydroxide filling said plurality of pores is in gel form.

13. The color containing silica of claim 8 wherein said dyed fixed aluminum hydroxide filling said plurality of pores is in gel form.

14. The color containing silica of claim 9 wherein said dyed fixed aluminum hydroxide filling said plurality of pores is in gel form.

15. The color containing silica of claim 8 wherein said silicate comprises sodium aluminosilicate.

16. The color containing silica of claim 1 wherein said plurality of silica particles comprise a lake pigment in said filled pores.

17. The color containing silicate of claim 1 wherein said dye comprises a FD&C dye.

\* \* \* \* \*